US00PP35833P2

(12) United States Plant Patent
Mathey

(10) Patent No.: US PP35,833 P2
(45) Date of Patent: May 28, 2024

(54) ***LEUCOTHOE* PLANT NAMED 'SMNLFGRV'**

(50) Latin Name: *Leucothoe fontanesiana*
Varietal Denomination: SMNLFGRV

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/239,890

(22) Filed: Aug. 30, 2023

(51) Int. Cl.
*A01H 5/02* (2018.01)
*A01H 6/36* (2018.01)

(52) U.S. Cl.
USPC ..... Plt./226
CPC ..... *A01H 6/36* (2018.05)

(58) Field of Classification Search
USPC ..... Plt./226
CPC ..... A01H 6/36; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Leucothoe* plant named 'SMNLFGRV', characterized by its upright to outwardly spreading and mounding plant habit; vigorous growth habit and rapid growth rate; freely branching habit; dense and bushy appearance; leaves that are dark green and light yellow variegated that become tinged with reddish orange in the late summer and autumn; numerous white-colored campanulate flowers; and good garden performance.

3 Drawing Sheets

Figure 1:
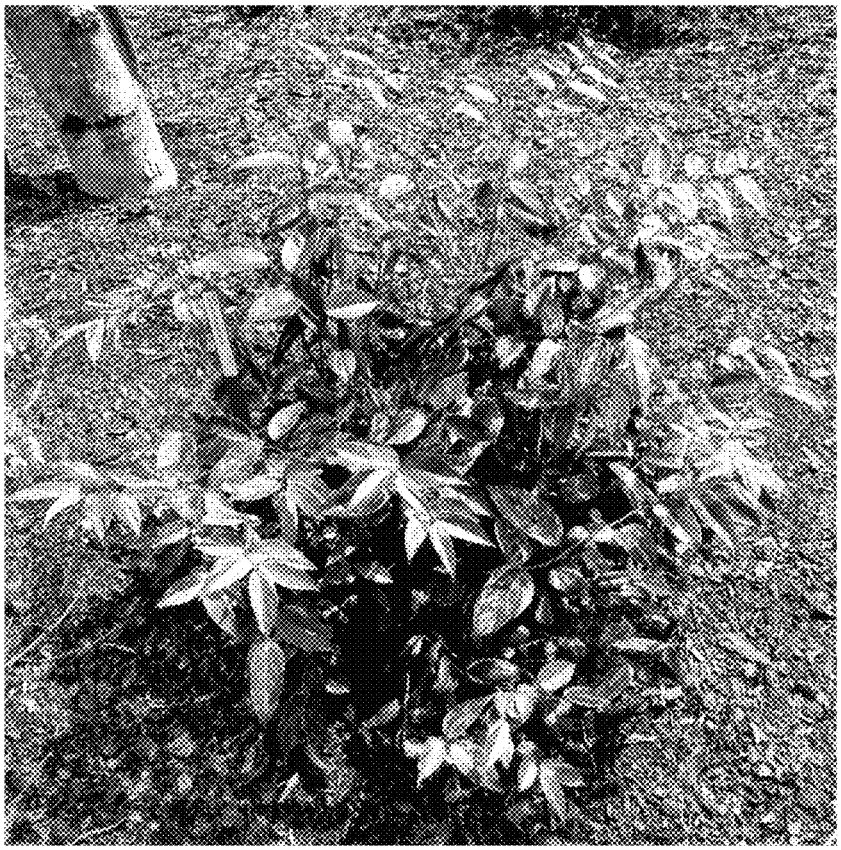

Botanical designation: *Leucothoe fontanesiana.*
Cultivar denomination: 'SMNLFGRV'.

BACKGROUND OF THE INVENTION

The present invention relates to a new and distinct cultivar of *Leucothoe* plant, botanically known as *Leucothoe fontanesiana*, commonly referred to as Highland or Mountain Doghobble and hereinafter referred to by the cultivar name 'SMNLFGRV'.

The new *Leucothoe* is a product of a planned breeding program conducted by the Inventor in Grand Haven, Michigan. The objective of the breeding program was to develop new freely branching *Leucothoe* plants with attractive and intense leaf variegation.

The new *Leucothoe* plant originated from an open-pollination in 2015 on Grand Haven, Michigan of *Leucothoe fontanesiana* 'Giards Rainbow', not patented, as the female, or seed, parent with an unknown selection of *Leucothoe fontanesiana* as the male, or pollen, parent. The new *Leucothoe* plant was discovered and selected by the Inventor in 2016 as a single flowering plant within the progeny of the stated open-pollination in a controlled environment in Grand Haven, Michigan.

Asexual reproduction of the new *Leucothoe* plant by softwood stem cuttings in a controlled greenhouse environment in Grand Haven, Michigan since 2016 has shown that the unique features of this new *Leucothoe* plant are stable and reproduced true to type in successive generations of asexual reproduction.

SUMMARY OF THE INVENTION

Plants of the new *Leucothoe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNLFGRV'. These characteristics in combination distinguish 'SMNLFGRV' as a new and distinct *Leucothoe* plant:

1. Upright to outwardly spreading and mounding plant habit.
2. Vigorous growth habit and rapid growth rate.
3. Freely branching habit; dense and bushy appearance.
4. Leaves that are dark green and light yellow variegated that become tinged with reddish orange in the late summer and autumn.
5. Numerous white-colored campanulate flowers.
6. Good garden performance.

Plants of the new *Leucothoe* can be compared to plants of the female parent, 'Giards Rainbow'. In side-by-side comparisons, plants of the new *Leucothoe* differ primarily from plants of 'Giards Rainbow' in leaf color as leaves of the new *Leucothoe* are dark green and light yellow variegated whereas leaves of plants of 'Giards Rainbow' are green and dark yellow variegated. In addition, leaf variegation is more stable on plants of the new *Leucothoe* than plants of 'Giards Rainbow'.

Plants of the new *Leucothoe* can also be compared to plants of *Leucothoe axillaris* 'Dodd's Variegated', not patented. In side-by-side comparisons, plants of the new *Leucothoe* differ primarily from plants of 'Dodd's Variegated' in leaf color as leaves of the new *Leucothoe* are dark green and light yellow variegated whereas leaves of plants of 'Dodd's Variegated' are mostly green with fewer cream-colored sectors. In addition, when exposed to cold temperatures, developed leaves of the new *Leucothe* become tinged with dark pink to purple whereas leaves of plants of 'Dodd's Variegated' do not become tinged with dark pink to purple when exposed to cold temperatures.

BRIEF DESCRIPTION OF THE PHOTOGRAPHS

The accompanying colored photographs illustrate the overall appearance of the new *Leucothoe* plant showing the colors as true as it is reasonably possible to obtain in colored reproductions of this type. Colors in the photographs may differ slightly from the color values cited in the detailed botanical description which accurately describe the colors of the new *Leucothoe* plant.

The photograph on the first sheet (FIG. 1) is a top perspective view of a typical plant of 'SMNLFGRV' grown in an outdoor nursery.

Figure 2:
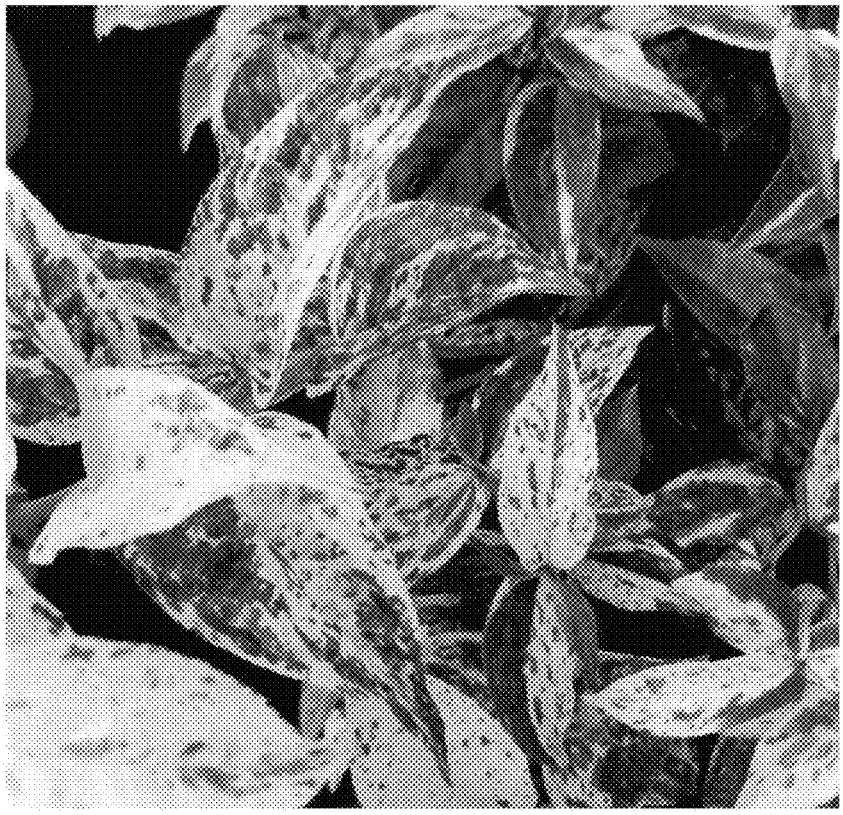

The photograph on the second sheet (FIG. 2) is a close-up view of a typical plant of 'SMNLFGRV'.

Figure 3:
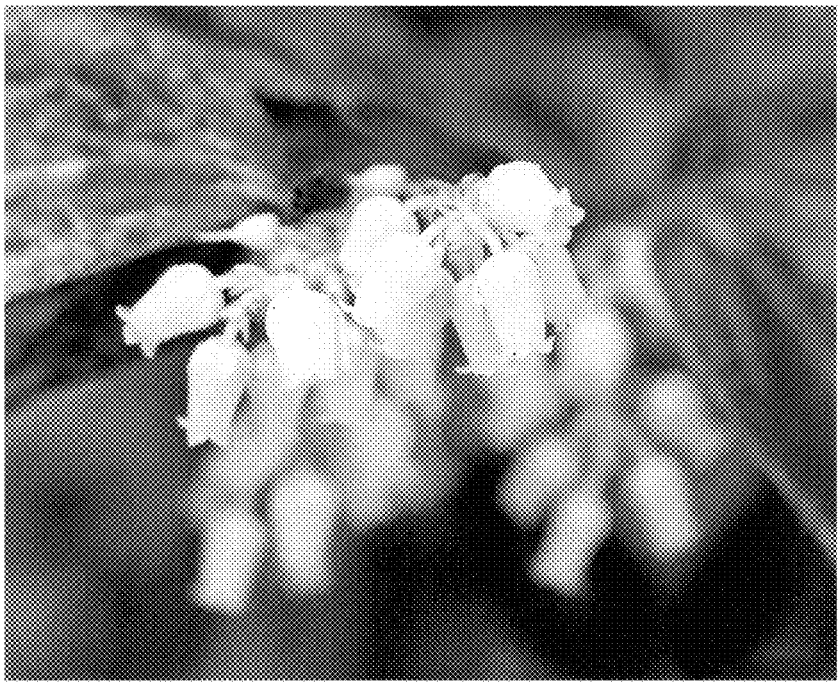

The photograph on the third sheet (FIG. 3) is close-up view of a typical inflorescence of 'SMNLFGRV'. Plants used for the photographs were about three years old.

DETAILED BOTANICAL DESCRIPTION

The following observations, measurements and values describe plants grown in the early summer in three-gallon containers in a polyethylene-covered greenhouse in Grand Haven, Michigan and under cultural practices typical of commercial *Leucothoe* production. During the production of the plants, day temperatures ranged from 18C to 27C and night temperatures ranged from 5C to 10C. Plants were three years old when the photographs were taken and two years old when the description was taken. In the description, color references are made to The Royal Horticultural Society Colour Chart, 2015 Edition, except where general terms of ordinary dictionary significance are used.

Botanical classification: *Leucothoe fontanesiana* 'SMNLFGRV'.

Parentage:

*Female, or seed, parent.*—*Leucothoe fontanesiana* 'Giards Rainbow', not patented.

*Male, or pollen, parent.*—Unknown selection of *Leucothoe fontanesiana*, not patented.

Propagation:

*Type.*—By softwood stem cuttings.

*Time to initiate roots, summer.*—About one to two weeks at temperatures about 18C to 27C.

*Time to produce a rooted young plant, summer.*—About six to seven weeks at temperatures about 18C to 27C.

*Root description.*—Fine and fibrous; typically brown in color, actual color of the roots is dependent on substrate composition, water quality, fertilizer, substrate temperature and physiological age of roots.

*Rooting habit.*—Moderately to freely branching; medium density.

Plant description:

*Plant form and growth habit.*—Perennial deciduous shrub; upright to outwardly spreading and mounding plant habit; vigorous growth habit and rapid growth rate.

*Branching habit.*—Freely branching habit; about 20 lateral branches develop per plant; pinching enhances lateral branch development.

*Plant height.*—About 35 cm.

*Plant diameter* (*area of spread*).—About 40 cm.

Lateral branch description:

*Length.*—About 30 cm.

*Diameter.*—About 5 mm.

*Internode length.*—About 3 cm.

*Aspect.*—About 45 to 60 degrees from vertical.

*Strength.*—Strong.

*Texture.*—Smooth, glabrous.

*Color, developing and developed.*—Close to 144A and distally, close to 176A.

Leaf description:

*Arrangement.*—Alternate, simple.

*Length.*—About 8 cm.

*Width.*—About 3 cm.

*Shape.*—Lanceolate.

*Apex.*—Acuminate.

*Base.*—Obtuse.

*Margin.*—Ciliate.

*Texture, upper surface.*—Smooth, glabrous; coriaceous.

*Texture, lower surface.*—Smooth, glabrous; coriaceous; with prominent midrib.

*Venation pattern.*—Pinnate.

*Color.*—Developing leaves, upper surface: Close to 166B and centers, tinged with close to 144B. Developing leaves, lower surface: Close to 174C and centers, tinged with close to 144B. Fully expanded leaves, upper surface: Close to NN137A and 10C variegation; venation, close to 144B; with subsequent development, tinged with close to 176A. Fully expanded leaves, lower surface: Close to NN137B and 10D variegation; venation, close to 144B.

*Petioles.*—Length: About 1 cm. Diameter: About 2 mm. Texture, upper and lower surfaces: Slightly pubescent. Color, upper and lower surfaces: Close 144B.

Flower description:

*Flower appearance and arrangement.*—Campanulate flowers arranged in terminal racemes; freely flowering habit with about 18 to 22 flowers per inflorescence with numerous inflorescences developing per plant; flowers drooping.

*Fragrance.*—If present, faint and pleasant.

*Natural flowering season.*—Plants flower continuously in April and May in Michigan; flowers not persistent.

*Inflorescence diameter.*—About 4 cm.

*Inflorescence height.*—About 1.5 cm.

*Flower diameter.*—About 3 mm.

*Flower length.*—About 5 mm.

*Flower buds.*—Length: About 3 mm. Diameter: About 1.5 mm. Shape: Oblong. Color: Close to 145C.

*Petals.*—Quantity and arrangement: Five fused with apices free. Length: About 4 mm. Width: About 4 mm. Shape: Roughly deltoid. Apex: Acute. Margin: Entire. Texture, upper and lower surfaces: Smooth, silky; glabrous. Color: When opening and fully opened, upper surface: Close to 157C. When opening and fully opened, lower surface: Close to 157C.

*Sepals.*—Quantity and arrangement: Five in a single whorl fused at the base. Length: About 2 mm. Width: About 1 mm. Shape: Oblong. Apex: Acute. Margin: Entire. Texture, upper and lower surfaces: Smooth, glabrous. Color, upper and lower surfaces: Close to NN155A and at the apices, close to 145C.

*Peduncles.*—Length: About 2.5 cm. Diameter: About 2 mm. Aspect: About 90 degrees from vertical. Strength: Strong. Texture: Smooth, glabrous. Color, upper and lower surfaces: Close to NN155A.

*Pedicels.*—Length: About 2 mm. Diameter: About 1 mm. Aspect: About 45 degrees from peduncle axis. Strength: Strong. Texture: Smooth, glabrous. Color, upper and lower surfaces: Close to NN155A.

*Reproductive organs.*—Stamens: Quantity per flower: Eight. Filament length: About 1 mm. Filament color: Close to NN155A. Anther length: Less than 0.5 mm. Anther shape: Rounded. Anther color: Close to 175B. Pollen amount: Scarce. Pollen color: Close to 162B. Pistils: Quantity per flower: One. Pistil length: About 4 mm. Stigma shape: Peltate. Stigma color: Close to N144A. Style length: About 3 mm. Style color: Close to NN155A.

*Fruits and seeds.*—To date, fruit and seed development have not been observed on plants of the new *Leucothoe*.

Garden performance: Plants of the new *Leucothoe* have been observed to have good garden performance and tolerate temperatures ranging from −31C to 38C.

Pathogen & pest resistance: To date, plants of the new *Leucothoe* have not been shown to be resistant to pathogens and pests common to *Leucothoe* plants.

It is claimed:

1. A new and distinct *Leucothoe* plant named 'SMNLFGRV' as illustrated and described.

* * * * *